US012765846B2

(12) United States Patent
Giebel et al.

(10) Patent No.: US 12,765,846 B2
(45) Date of Patent: Oct. 20, 2026

(54) COMPUTED TOMOGRAPHY DEVICE WITH A BODY SUPPORT APPARATUS INCLUDING A BOARD MOUNTED PIVOTABLY ABOUT AN AXIS

(71) Applicant: Siemens Healthineers AG, Forchheim (DE)

(72) Inventors: Steffen Giebel, Wiesenthau (DE); Martin Ramsauer, Pyrbaum (DE); Jens Fehre, Hausen (DE); Marco Koehler, Adelsdorf (DE); Jens Herbolzheimer, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 170 days.

(21) Appl. No.: 18/342,926

(22) Filed: Jun. 28, 2023

(65) Prior Publication Data

US 2024/0000400 A1 Jan. 4, 2024

(30) Foreign Application Priority Data

Jun. 30, 2022 (EP) .................................... 22182323

(51) Int. Cl.

*A61B 6/03* (2006.01)
*A61B 6/04* (2006.01)
*A61B 6/00* (2006.01)

(52) U.S. Cl.

CPC ............ *A61B 6/035* (2013.01); *A61B 6/0442* (2013.01); *A61B 6/4447* (2013.01)

(58) Field of Classification Search

None

See application file for complete search history.

(56) References Cited

U.S. PATENT DOCUMENTS

| | | | | |
|---|---|---|---|---|
| 7,600,281 | B2 * | 10/2009 | Skripps | A61G 13/10 5/624 |
| 10,568,560 | B2 * | 2/2020 | Mukdadi | A61B 6/4417 |
| 2005/0135560 | A1 | 6/2005 | Dafni | |
| 2005/0204473 | A1 * | 9/2005 | Maier | A61B 6/04 5/601 |

(Continued)

FOREIGN PATENT DOCUMENTS

| | | | |
|---|---|---|---|
| CN | 1663532 | A | 9/2005 |
| CN | 201958896 | U | 9/2011 |

(Continued)

*Primary Examiner* — Tahmina N Ansari

(74) *Attorney, Agent, or Firm* — Harness, Dickey & Pierce, P.L.C.

(57) ABSTRACT

A computed tomography device has a gantry with an opening and a body support apparatus to support a body of a person, the body support apparatus has a board and is arranged relative to the opening such that a shoulder region of the body of the person rests on the board when the board is in an examination position of the board relative to the gantry and the head of the person is inserted into the opening along a system axis of the gantry, the body support apparatus has a pivoting apparatus and the board is mounted pivotably about a pivot axis relative to the gantry via the pivoting apparatus such that a first pivoting movement of the board about the pivot axis can move the board relative to the gantry from a preparation position of the board to the examination position of the board.

20 Claims, 8 Drawing Sheets

(56) References Cited

U.S. PATENT DOCUMENTS

| | | | | |
|---|---|---|---|---|
| 2006/0248650 | A1* | 11/2006 | Skripps | A61G 13/0054 5/624 |
| 2008/0005844 | A1 | 1/2008 | Tybinkowski et al. | |
| 2010/0205740 | A1 | 8/2010 | Tybinkowski | |
| 2013/0044855 | A1* | 2/2013 | Laukkanen | A61B 6/035 378/4 |
| 2014/0053333 | A1* | 2/2014 | Krieg | A61B 6/487 5/601 |
| 2014/0275953 | A1* | 9/2014 | Gregerson | A61B 6/4405 600/407 |
| 2014/0276018 | A1* | 9/2014 | Mukdadi | A61B 6/4208 600/426 |
| 2014/0276019 | A1* | 9/2014 | Majewski | G01T 1/2985 600/425 |
| 2016/0242705 | A1 | 8/2016 | Richardson | |
| 2017/0189720 | A1* | 7/2017 | Liu | A61N 5/1081 |
| 2017/0319152 | A1 | 11/2017 | Laukkanen et al. | |
| 2018/0271459 | A1 | 9/2018 | Wang et al. | |
| 2019/0313985 | A1 | 10/2019 | Bardo et al. | |
| 2019/0357862 | A1 | 11/2019 | Bailey et al. | |
| 2020/0022611 | A1* | 1/2020 | Nelson | A61B 5/704 |
| 2020/0187873 | A1 | 6/2020 | Lautenschlaeger | |
| 2021/0315530 | A1 | 10/2021 | DeLong Samalik et al. | |
| 2021/0369214 | A1* | 12/2021 | Achleitner | A61B 6/4452 |
| 2021/0386386 | A1 | 12/2021 | Bailey et al. | |
| 2024/0000400 | A1* | 1/2024 | Giebel | A61B 6/035 |

FOREIGN PATENT DOCUMENTS

| | | | |
|---|---|---|---|
| CN | 202235424 | U | 5/2012 |
| CN | 102933151 | A | 2/2013 |
| CN | 103622790 | A | 3/2014 |
| CN | 104939923 | A | 9/2015 |
| CN | 106924888 | A | 7/2017 |
| CN | 108882910 | A | 11/2018 |
| CN | 110403623 | A | 11/2019 |
| CN | 111297385 | A | 6/2020 |
| CN | 210990362 | U | 7/2020 |
| CN | 112996443 | A | 6/2021 |
| CN | 113040809 | A | 6/2021 |
| CN | 113424068 | A | 9/2021 |
| CN | 113520445 | A | 10/2021 |
| CN | 214907116 | U | 11/2021 |
| CN | 113729746 | A | 12/2021 |
| DE | 102020206784 | A1 | 7/2021 |
| EP | 3287112 | A1 | 2/2018 |
| EP | 2600770 | B1 | 9/2018 |
| JP | S6337929 | Y2 | 10/1988 |
| WO | WO 2020106402 | A1 | 5/2020 |

* cited by examiner

COMPUTED TOMOGRAPHY DEVICE WITH A BODY SUPPORT APPARATUS INCLUDING A BOARD MOUNTED PIVOTABLY ABOUT AN AXIS

CROSS-REFERENCE TO RELATED APPLICATION(S)

The present application claims priority under 35 U.S.C. § 119 to European Patent Application No. 22182323.0, filed Jun. 30, 2022, the entire contents of which are incorporated herein by reference.

FIELD

One or more example embodiments relates to a computed tomography device with a body support apparatus for supporting a body of a person. One or more example embodiments further relates to a medical imaging system and a method for arranging a board of a body support apparatus relative to a gantry of a computed tomography device.

RELATED ART

In an examination performed using an imaging device, it may be necessary for a first body region of a person to be temporarily supported by the imaging device while simultaneously a second body region of the person rests on a patient bed that is separate from the imaging device. For example, when a head is imaged via a head computed tomography device, the patient support can be divided between the head computed tomography device and a patient bed such that the head computed tomography device supports a first body region including the head and the shoulder region and the patient bed supports a second body region including the pelvic region and legs. An appropriate body support apparatus may be used to enable this divided patient support and for switching between the divided patient support and a patient support that is resting entirely on the patient bed in a safe and stable manner. Both the imaging device and the patient bed can be of mobile design.

SUMMARY

Such a body support apparatus should be compatible with the mobility of the imaging device and of the patient bed, in particular relative to one another, at least in the sections of the clinical workflow that provide for such mobility.

One or more example embodiments provides an imaging device which is improved with respect to a patient support that is divided between the imaging device and a patient bed. The subject matter of each of the independent claims achieves this object. The dependent claims take account of further advantageous aspects of one or more example embodiments.

BRIEF DESCRIPTION OF THE DRAWINGS

In the following, the invention is explained with reference to exemplary embodiments and with reference to the attached figures. The depiction in the figures is schematic, greatly simplified and is not necessarily true to scale.

DETAILED DESCRIPTION

Figure 1:
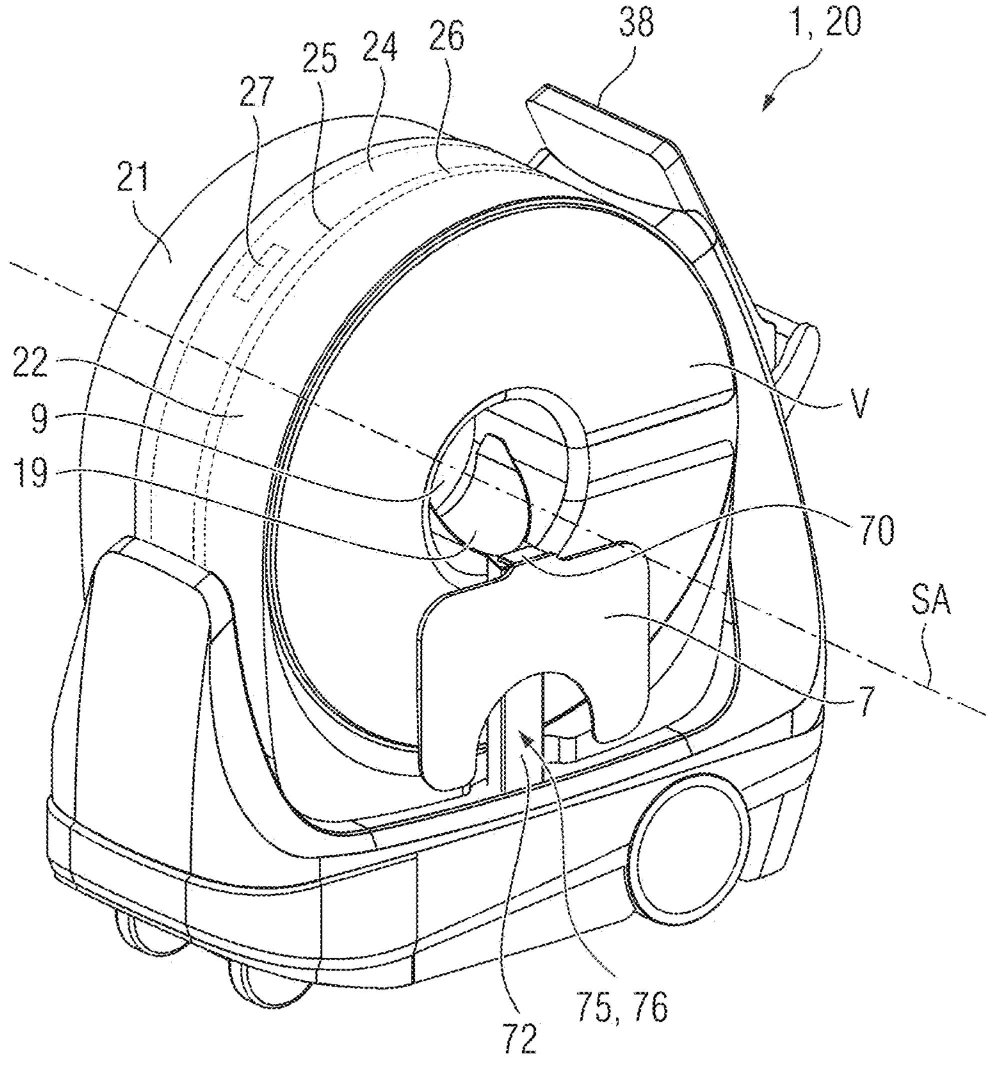
FIG. 1 shows a computed tomography device with a gantry and a body support apparatus according to one or more example embodiments.

One or more example embodiments relates to a computed tomography device having a gantry with an opening and a body support apparatus for supporting a body of a person, wherein the body support apparatus has a board and is arranged relative to the opening such that a shoulder region of the body of the person rests on the board, when the board is in an examination position of the board relative to the gantry, and the head of the person is inserted into the opening along a system axis of the gantry, characterized in that the body support apparatus has a pivoting apparatus and the board is mounted pivotably about a pivot axis relative to the gantry via the pivoting apparatus such that a first pivoting movement of the board about the pivot axis can move the board relative to the gantry from a preparation position of the board to the examination position of the board.

The computed tomography device can in particular be embodied as a head computed tomography device and/or as a mobile computed tomography device.

In particular, it can be provided that the person can be moved along the system axis of the gantry relative to the gantry, in particular can be carried by medical staff, in order thereby to insert the head of the person into the opening when the board is in the examination position of the board.

In particular, it can be provided that the board is mounted pivotably about the pivot axis relative to the gantry via the pivoting apparatus such that a second pivoting movement of the board about the pivot axis can move the board relative to the gantry from the examination position of the board to the preparation position of the board. In particular, the second pivoting movement of the board about the pivot axis can cause the board to be raised from the examination position to the preparation position.

The board can in particular be embodied as dimensionally stable and/or plate-shaped. The opening can, for example, be tunnel-shaped and/or extend along the system axis. The system axis can, for example, run through the opening, in particular through a central region of the opening. The system axis can, for example, run through an isocenter of the computed tomography device. The pivoting apparatus can in particular be a pivot bearing and/or embodied in the form of a folding mechanism.

One embodiment provides that the body support apparatus further has a locking system, wherein the locking system is configured to lock the board in the preparation position of the board relative to the gantry and/or to lock the board in the examination position of the board relative to the gantry.

The locking system can in particular be configured to secure the board in a positive-fitting and/or non-positive-fitting manner against lowering and/or against raising when the board is in the preparation position. The locking system can in particular be configured to secure the board in a positive-fitting and/or non-positive-fitting manner against lowering and/or against raising when the board is in the examination position. The locking system can in particular be configured to secure the board in a positive-fitting and/or non-positive-fitting manner against lowering and/or against raising when the board is in the transport position.

One embodiment provides that the body support apparatus further has a damper for braking the first pivoting movement of the board relative to the gantry. The damper can, for example, be integrated into the pivoting apparatus. The damper can, for example, be a rotary damper and/or a torsion spring.

One embodiment provides that the system axis is substantially horizontal, in particular horizontal, and/or that the pivot axis is substantially horizontal, in particular horizontal.

One embodiment provides that the pivot axis is located below the system axis with respect to a vertical direction. In particular, the pivot axis can be located at the height of a lower edge of the opening with respect to the vertical direction.

One embodiment provides that the board extends in a planar manner in a board plane and/or that the board plane is substantially parallel to the pivot axis. In particular, it can be provided that the board extends in a planar manner between a bed-side edge of the board and a gantry-side edge of the board, in particular when the board is in the examination position. In particular, the gantry-side edge of the board can be arranged on the pivot axis. The bed-side edge of the board can in particular be located on a side of the board facing away from the pivot axis.

One embodiment provides that the board plane is substantially perpendicular to the system axis, in particular perpendicular, when the board is in the preparation position of the board.

One embodiment provides that the board projects away from the opening when the board is in the examination position of the board. In particular, it can be provided that an angle between the board plane and the system axis is less than 45 degrees, for example less than 20 degrees, in particular less than 10 degrees, when the board is in the examination position of the board.

One embodiment provides that the first pivoting movement of the board about the pivot axis causes the board to be lowered, in particular causes the board to be lowered from the preparation position to the examination position.

Furthermore, it can be provided that the board is mounted pivotably about the pivot axis relative to the gantry via the pivoting apparatus such that a preparatory pivoting movement of the board about the pivot axis can move the board relative to the gantry from a transport position of the board to the preparation position of the board. In particular, it can be provided that the preparatory pivoting movement of the board about the pivot axis causes the board to be raised, in particular causes the board to be raised from the transport position to the preparation position.

Furthermore, it can be provided that the gantry has an interior region and a cladding for delimiting the interior region from an environment and that the board rests on a region of the cladding when the board is in the transport position of the board relative to the gantry. In particular, it can be provided that the board plane is substantially perpendicular to the system axis when the board is in the transport position of the board relative to the gantry. As a result, the space requirement of the gantry can be reduced, in particular in order to perform a transport movement of the gantry.

In particular, it can be provided that the board is mounted pivotably about the pivot axis relative to the gantry via the pivoting apparatus such that a third pivoting movement of the board about the pivot axis can move the board relative to the gantry from the preparation position of the board to the transport position of the board. In particular, the third pivoting movement of the board about the pivot axis can cause the board to be lowered from the preparation position to the transport position. In particular, the damper can further be configured to brake the third pivoting movement of the board relative to the gantry.

One embodiment provides that the body support apparatus further has a holding apparatus, wherein the pivoting apparatus is connected to the gantry via the holding apparatus, wherein the board is connected to the holding apparatus via the pivoting apparatus and is mounted pivotably about the pivot axis relative to the holding apparatus, wherein the holding apparatus is configured to set a distance between the pivot axis and the system axis in an adjustable manner, in particular in a stepped or infinitely adjustable manner.

The holding apparatus can in particular be configured to set the distance between the pivot axis and the system axis in a variable manner by setting a height at which the pivot axis runs with respect to the vertical direction, wherein the height of the system axis remains unchanged with respect to the vertical direction. For this purpose, the holding apparatus can, for example, be telescopic. The holding apparatus can, for example, have a locking apparatus in order to maintain the set distance between the pivot axis and the system axis.

In particular, it can be provided that the holding apparatus rests relative to the gantry during the first pivoting movement of the board about the pivot axis and/or that the holding apparatus rests relative to the gantry during the preparatory pivoting movement of the board about the pivot axis. In particular, it can be provided that the holding apparatus rests relative to the gantry during the second pivoting movement of the board about the pivot axis and/or that the holding apparatus rests relative to the gantry during the third pivoting movement of the board about the pivot axis.

One embodiment provides that the gantry has a first gantry part and a second gantry part, wherein the first gantry part has a rotatably mounted rotor with a projection data acquisition system, wherein the second gantry part has at least one section of the opening, wherein the board is connected to the second gantry part via the pivoting apparatus and is mounted pivotably about the pivot axis relative to the second gantry part. The projection data acquisition system can in particular have an X-ray source for generating X-rays and/or an X-ray detector, which, for example, interacts with the X-ray source and/or is configured to detect the X-rays.

Furthermore, it can be provided that the first gantry part is mounted movably relative to the second gantry part such that a translatory movement of the first gantry part relative to the second gantry part can be executed, while at the same time the second gantry part rests relative to the head of the person and the body support apparatus rests relative to the head of the person and relative to the at least one section of the opening when the head of the person is located in the opening.

In particular, it can be provided that the first gantry part has a pivot bearing and a support structure and that the rotor is connected to the support structure via the pivot bearing and is mounted rotatably about the system axis relative to the support structure.

One or more example embodiments further relates to a medical imaging system having the computed tomography device according to one or more example embodiments and a patient bed for supporting the person, wherein the patient bed can be arranged in an examination position of the patient bed relative to the gantry.

In particular, it can be provided that a pelvic region of the person rests on the patient bed and/or that a leg region of the person rests on the patient bed when the patient bed is in the examination position of the patient bed relative to the gantry, the board is in the examination position of the board relative to the gantry, the shoulder region of the body of the person rests on the board and the head of the person is introduced into the opening along a system axis of the gantry. In particular, the patient bed can be a mobile intensive care bed and/or an examination bench of a mobile stroke unit.

One embodiment provides that the board bridges a gap extending between the gantry and the patient bed substantially perpendicular to the system axis when the patient bed is in the examination position of the patient bed and the board is in the examination position of the board.

One embodiment provides that the body support apparatus is arranged relative to the gantry such that a bed-side edge of the board rests on the patient bed when the patient bed is in the examination position of the patient bed and the board is in the examination position of the board.

One or more example embodiments further relates to a method for arranging a board of a body support apparatus relative to a gantry of a computed tomography device according to one or more example embodiments, wherein the first pivoting movement of the board about the pivot axis moves the board relative to the gantry from the preparation position of the board to the examination position of the board.

Furthermore, it can be provided that a preparatory pivoting movement of the board about the pivot axis moves the board relative to the gantry from a transport position of the board to the preparation position of the board. The preparatory pivoting movement of the board about the pivot axis can, for example, cause the board to be raised, in particular cause the board to be raised from the transport position of the board to the preparation position of the board. The first pivoting movement of the board about the pivot axis can, for example, cause the board to be lowered, in particular cause the board to be lowered from the preparation position to the examination position.

Each of the described pivoting movements of the board about the pivot axis can, for example, take place in that the board is manually pivoted about the pivot axis in each case, in particular manually pivoted about the pivot axis by medical staff, in particular manually folded up or down.

Furthermore, it can be provided that the body support apparatus further has a pivot drive for driving the first pivoting movement and/or for driving the second pivoting movement. The pivot drive can, for example, be configured to exert a torque on the board with respect to the pivot axis.

In particular, it can be provided that the preparatory pivoting movement of the board about the pivot axis takes place while the patient bed is far enough away from the gantry to ensure that it does not interfere with the preparatory pivoting movement of the board about the pivot axis. Furthermore, it can be provided that a first translatory movement of the patient bed relative to the gantry takes place along the system axis in order to bring the patient bed into the examination position of the patient bed relative to the gantry while the board is in the preparation position of the board relative to the gantry. Furthermore, it can be provided that the first pivoting movement of the board about the pivot axis takes place while the patient bed is in the examination position of the patient bed relative to the gantry, in particular such that the first pivoting movement of the board about the pivot axis is limited by an impingement of the bed-side edge of the board on the patient bed.

Advantageously, the board can be folded down from an upwardly inclined preparation position onto the patient bed without interference from the patient bed even if the patient bed is close to the gantry.

Furthermore, it can be provided that the second pivoting movement of the board about the pivot axis takes place while the patient bed is in the examination position of the patient bed relative to the gantry. Furthermore, it can be provided that a second translatory movement of the patient bed relative to the gantry takes place along the system axis in order to remove the patient bed from the gantry while the board is in the preparation position of the board relative to the gantry. In particular, it can be provided that the third pivoting movement of the board about the pivot axis takes place while the patient bed is far enough away from the gantry to ensure that it does not interfere with the third pivoting movement of the board about the pivot axis.

One or more example embodiments enables the implementation of a divided patient support in a stable and safe manner, wherein better account can be taken of patient-specific anatomical features and/or features of the patient bed, in particular relating to the bed height, compared to conventional solutions. Further, in order to correct the examination position of the patient bed relative to the gantry, the board can be folded up about the pivot axis and folded down again when the correction has been made. This is less labor-intensive for the medical staff than completely detaching the board from the gantry and reconnecting it after the correction.

Within the scope of the invention, features described with respect to different embodiments of the invention and/or different claim categories (method, use, apparatus, system, arrangement etc.) may be combined to form further embodiments of the invention. For example, a claim relating to an apparatus can also be developed with features described or claimed in connection with a method and vice versa. Herein, functional features of a method can be executed by correspondingly embodied substantive components. The use of the indefinite article "a" or "an" does not preclude the possibility of the feature in question also being present more than once.

FIG. 1 shows a computed tomography device 1 having a gantry 20 with an opening 9 and a body support apparatus 75 for supporting a body 15 of a person 13.

The body support apparatus 75 has a board 7 and is arranged relative to the opening 9 such that a shoulder region of the body 15 of the person 13 rests on the board 7, when the board 7 is in an examination position of the board 7 relative to the gantry 20, and the head 14 of the person 13 is introduced into the opening 9 along a system axis SA of the gantry 20. The body support apparatus 75 has a pivoting apparatus 70 and the board 7 is mounted pivotably about a pivot axis 7A relative to the gantry 20 via the pivoting apparatus 70 such that a first pivoting movement of the board 7 about the pivot axis 7A can move the board 7 relative to the gantry 20 from a preparation position of the board 7 to the examination position of the board 7.

The body support apparatus 75 further has a locking system 76, wherein the locking system 76 is configured to lock the board 7 in the preparation position of the board 7 relative to the gantry 20 and/or to lock the board 7 in the examination position of the board 7 relative to the gantry 20. The body support apparatus 75 further has a damper integrated into the pivoting apparatus 70 for braking the first pivoting movement of the board 7.

The body support apparatus 75 further has a holding apparatus 72, wherein the pivoting apparatus 70 is connected to the gantry 20 via the holding apparatus 72, wherein the board 7 is connected to the holding apparatus 72 via the pivoting apparatus 70 and is mounted pivotably about the pivot axis 7A relative to the holding apparatus 72, wherein the holding apparatus 72 is configured to set a distance between the pivot axis 7A and the system axis SA in an adjustable manner.

The gantry 20 has a first gantry part 21 and a second gantry part 22, wherein the first gantry part 21 has a rotatably mounted rotor 24 with a projection data acquisition system 27, wherein the second gantry part 22 has at least one section of the opening 9, wherein the board 7 is connected to the second gantry part 22 via the pivoting apparatus 70 and is mounted pivotably about the pivot axis 7A relative to the second gantry part 22.

The first gantry part 21 is mounted movably relative to the second gantry part 22 such that a translatory movement of the first gantry part 21 relative to the second gantry part 22 can be executed while at the same time the second gantry part 22 rests relative to the head 14 of the person 13 and the body support apparatus 75 rest relative to the head 14 of the person 13 and relative to the at least one section of the opening 9 when the head 14 of the person 13 is located in the opening 9.

The first gantry part 21 has a pivot bearing 25 and a support structure 26, wherein the rotor 24 is connected to the support structure 26 via the pivot bearing 25 and is mounted rotatably about the system axis SA relative to the support structure 26. The computed tomography device 1 further has a control unit 38 with a touch-sensitive screen.

FIGS. 2 to 7 show the computed tomography device 1 for different positions of a board 7 of the body support apparatus 75 relative to the gantry 20.

The system axis SA is horizontal and parallel to the horizontal direction z. The pivot axis 7A is horizontal and perpendicular to the horizontal direction z. The pivot axis 7A is located below the system axis SA with respect to the vertical direction y. The board 7 extends in a planar manner in a board plane 7E, wherein the board plane 7E is substantially parallel to the pivot axis 7A. The board plane 7E is in particular substantially perpendicular to the system axis SA when the board 7 is in the position according to FIG. 2 or in the position according to FIG. 3. The board 7 in particular projects from the opening 9 when the board 7 is in the position according to FIG. 5 or in the position according to FIG. 7.

Figure 3:
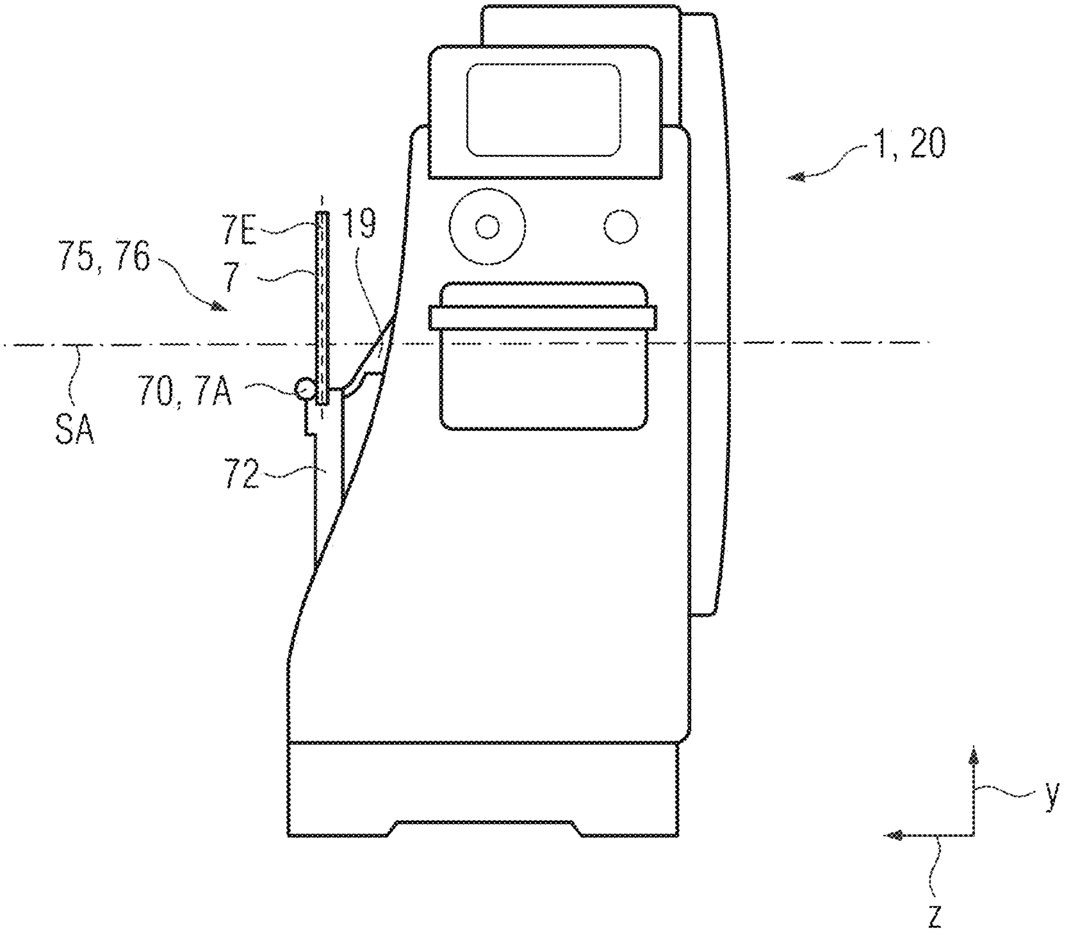
Figure 4:
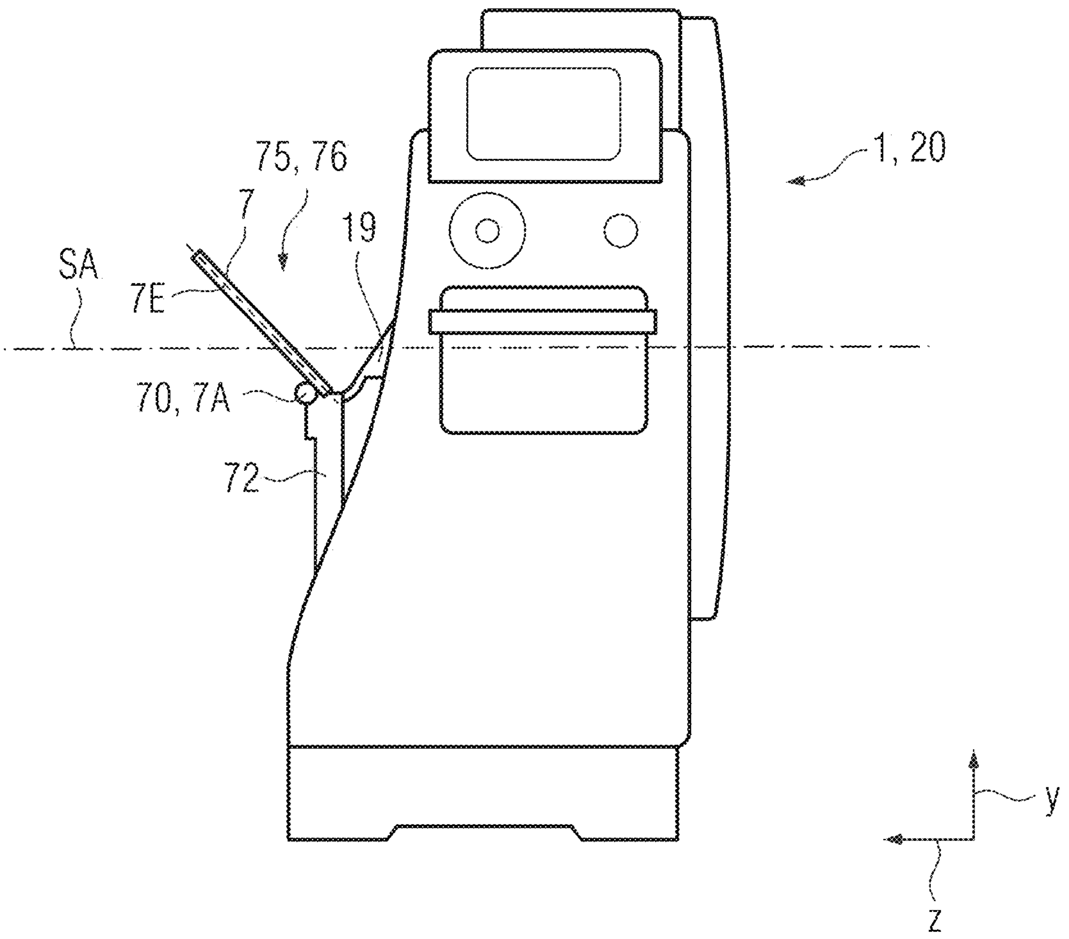
Figure 5:
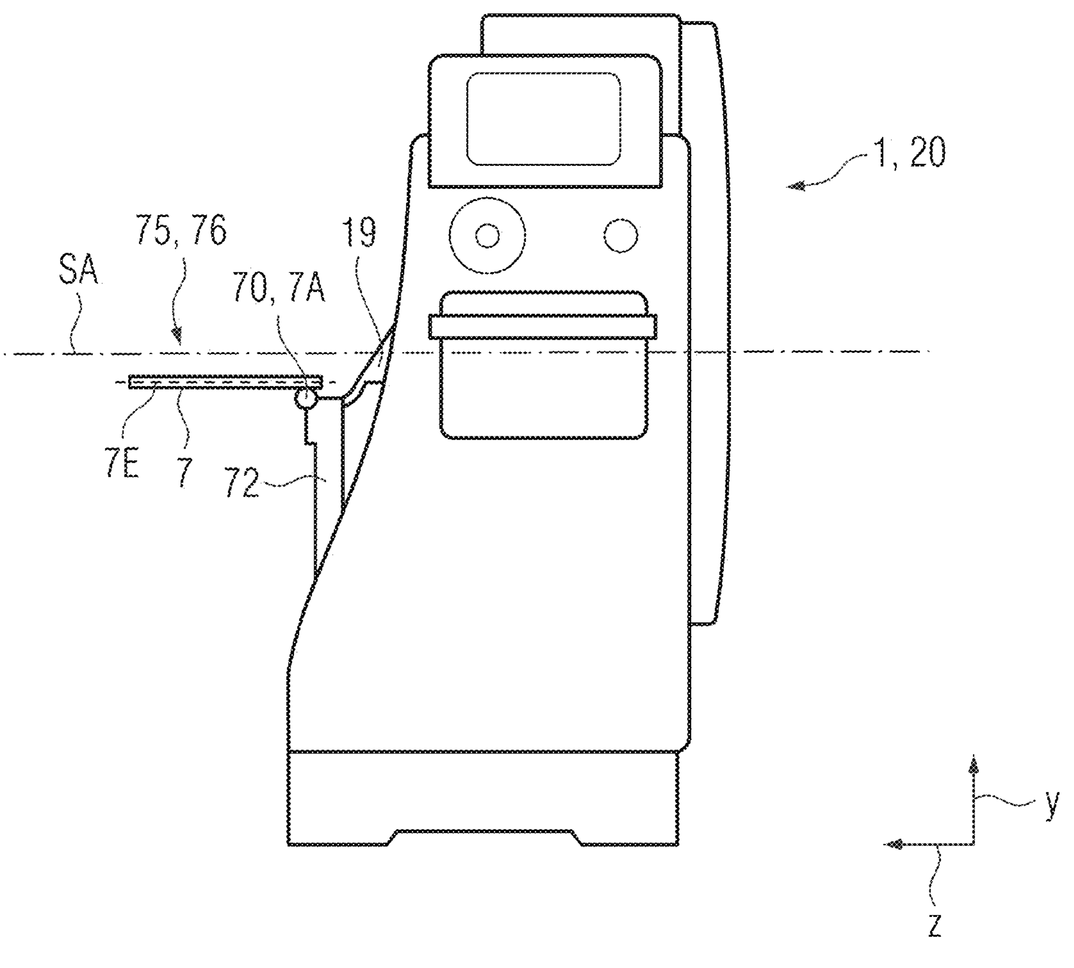
Figure 6:
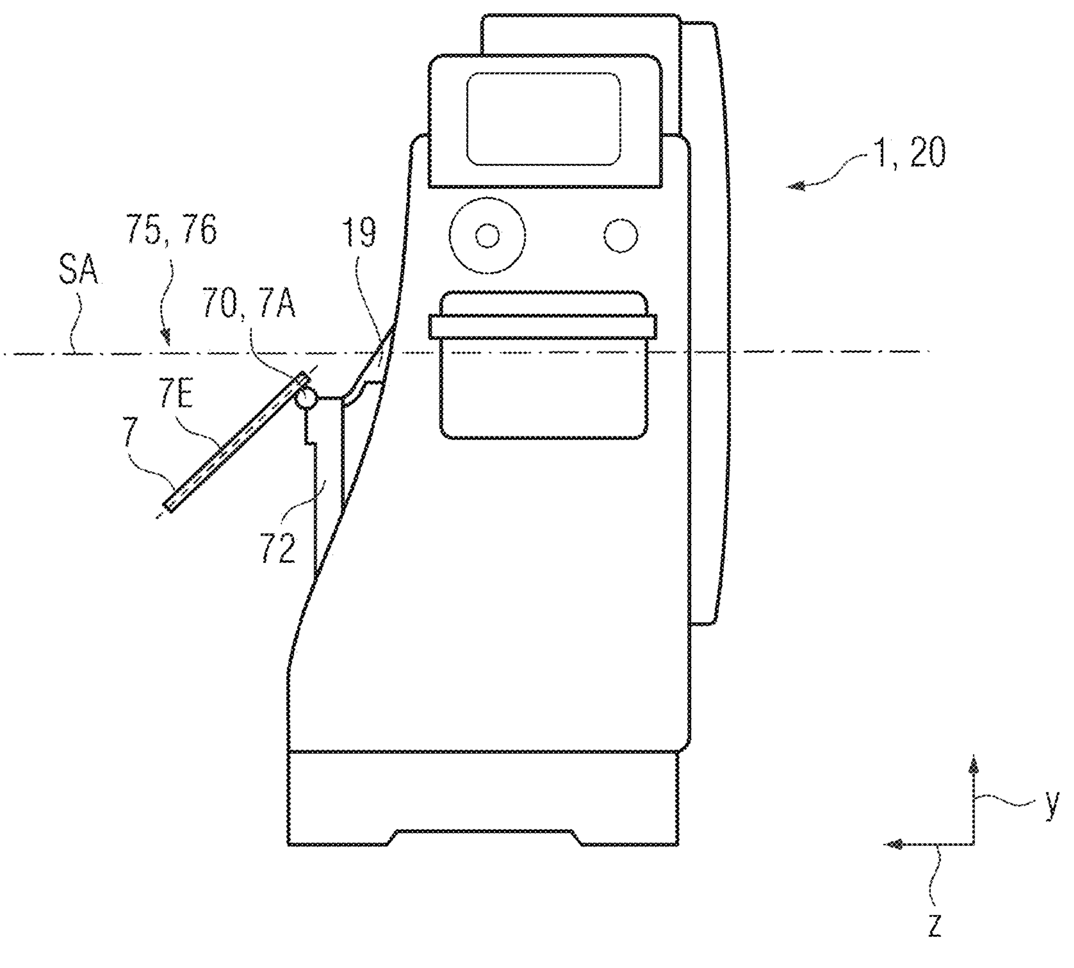

The first pivoting movement of the board 7 about the pivot axis 7A in particular causes the board 7 to be lowered when the first pivoting movement of the board 7 about the pivot axis 7A moves the board 7 from the position according to FIG. 3 to the position according to FIG. 5 or when the first pivoting movement of the board 7 about the pivot axis 7A moves the board 7 from the position according to FIG. 4 to the position according to FIG. 5.

Figure 2:
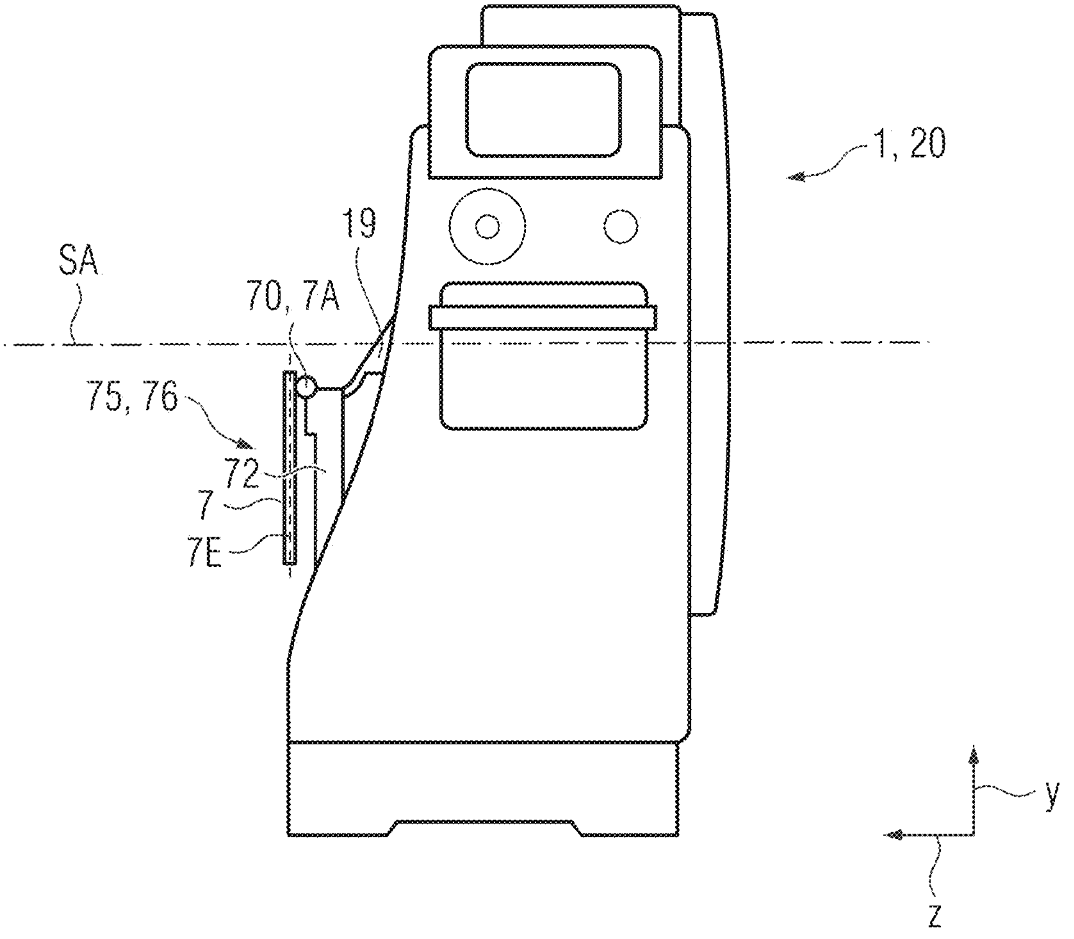
FIGS. 2 to 7 show the computed tomography device for different positions of a board of the body support apparatus relative to the gantry according to one or more example embodiments.

According to one exemplary embodiment, the position of the board 7 shown in FIG. 2 is the transport position of the board 7, the position of the board 7 shown in FIG. 3 is the preparation position of the board 7 and the position of the board 7 shown in FIG. 5 is the examination position of the board 7. According to another exemplary embodiment, the position of the board 7 shown in FIG. 3 is the transport position of the board 7, the position of the board 7 shown in FIG. 4 is the preparation position of the board 7 and the position of the board 7 shown in FIG. 5 is the examination position of the board 7. According to a further exemplary embodiment, the examination position of the board 7 is between the position of the board 7 shown in FIG. 5 and the position of the board 7 shown in FIG. 6.

Figure 7:
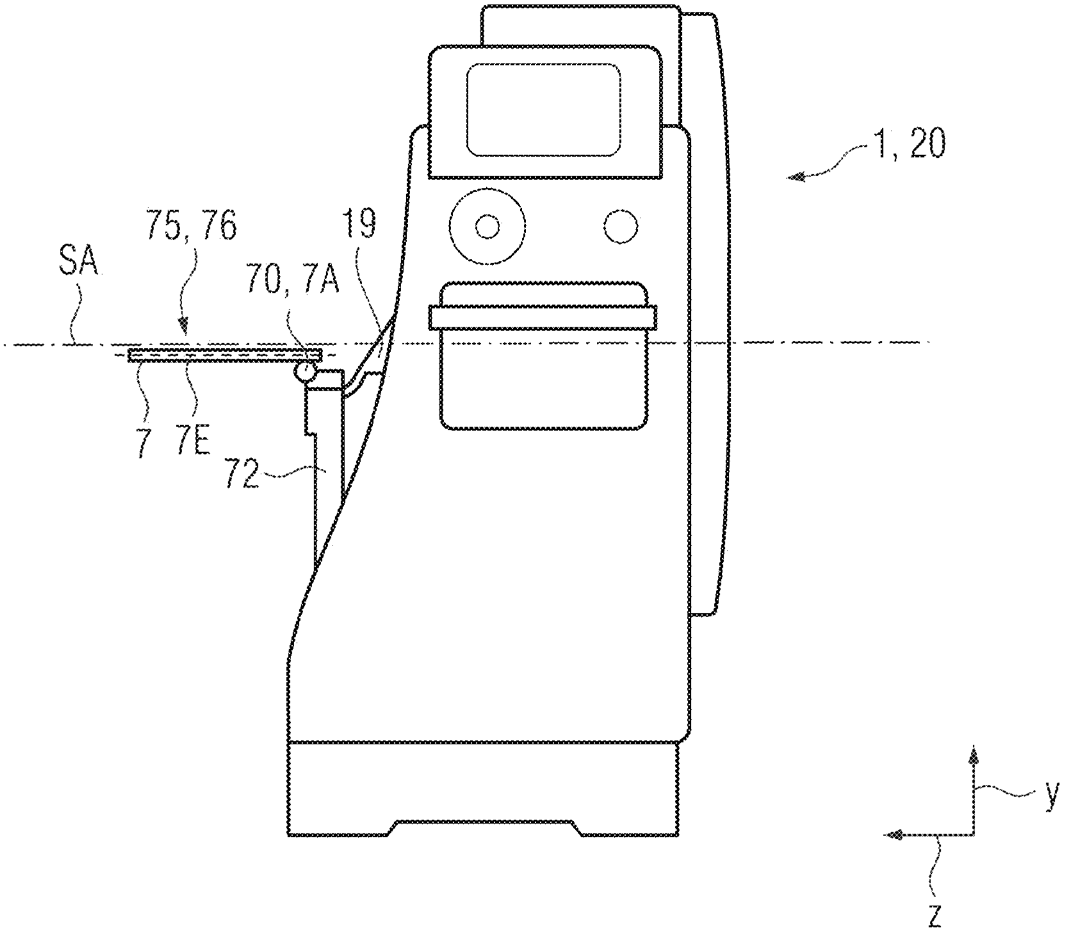

In FIG. 7, a height adjustment via the holding apparatus 72 results in the distance between the pivot axis 7A and the system axis SA being smaller than in FIG. 5. The height adjustment of the pivoting apparatus 70 has not changed the height of the head cup. According to another embodiment, a height adjustment of the head cup 19 relative to the system axis SA and/or relative to the pivot axis 7A is provided.

Figure 8:
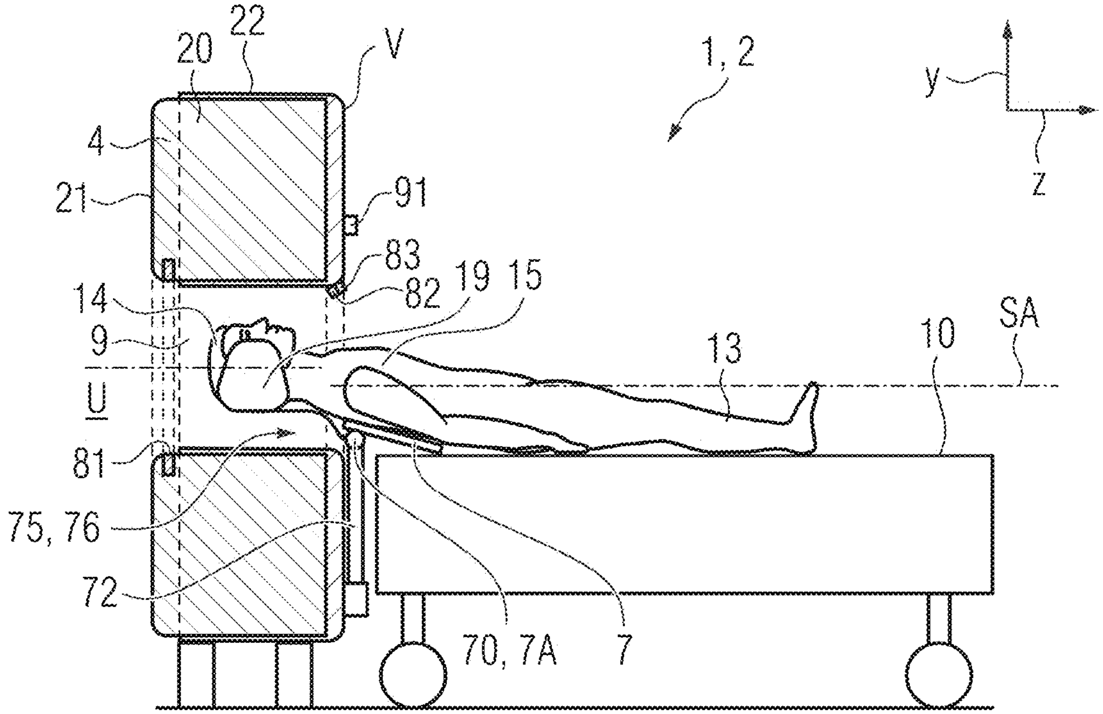
FIG. 8 shows a medical imaging system with a computed tomography device and a patient bed according to one or more example embodiments.

FIG. 8 shows a medical imaging system 2 having the computed tomography device 1 and a patient bed 10 for supporting the person 13, wherein the patient bed 10 is in an examination position of the patient bed 10 relative to the gantry 20 and the board 7 is in the examination position of the board 7. The computed tomography device 1 is a mobile head computed tomography device. The computed tomography device 1 has a head cup 19 that accommodates the head 14 of the person 13.

The board 7 bridges a gap extending between the gantry 20 and the patient bed 10 substantially perpendicular to the system axis SA. The body support apparatus 75 is arranged relative to the gantry 20 such that a bed-side edge of the board 7 rests on the patient bed 10. The board 7 also rests relative to the patient bed 10 when the translatory movement of the first gantry part 21 is executed relative to the second gantry part 22.

The gantry 20 has an interior region 4 and a cladding V for delimiting the interior region 4 from an environment U. The computed tomography device 1 has a radiation protection body 81 detachably connected to the gantry 20 such that it covers a rear side of the opening 9. The computed tomography device 1 has a radiation protection apparatus 91 for covering a front side of the opening 9, for example via a radiation protection curtain. The computed tomography device 1 further has a camera system 82 for patient observation and/or patient positioning and an acoustic system 83 for in particular bidirectional acoustic patient communication.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A computed tomography device comprising:

a gantry having an opening; and a body support apparatus configured to support a body of a person, the body support apparatus including a board, the body support apparatus being arranged relative to the opening such that, a shoulder region of the body of the person rests on the board based on the board being in an examination position of the board relative to the gantry and a head of the person being in the opening along a system axis of the gantry, the body support apparatus having a pivoting apparatus, the board being mounted pivotably about a pivot axis relative to the gantry via the pivoting apparatus such that a first pivoting movement of the board about the pivot axis moves the board relative to the gantry from a preparation position of the board to the examination position of the board, the board extending in a planar manner between a bed-side edge of the board and a gantry-side edge of the board, and the gantry-side edge of the board being on the pivot axis.

2. The computed tomography device of claim 1, wherein the body support apparatus includes a locking system; and the locking system is configured to at least one of, lock the board in the preparation position of the board relative to the gantry, or lock the board in the examination position of the board relative to the gantry.

3. The computed tomography device of claim 1, wherein the body support apparatus includes a damper configured to brake the first pivoting movement of the board.

4. The computed tomography device of claim 1, wherein the system axis is substantially horizontal; and the pivot axis is substantially horizontal.

5. The computed tomography device of claim 1, wherein the pivot axis is below the system axis with respect to a vertical direction.

6. The computed tomography device of claim 1, wherein the board extends in the planar manner in a board plane; and the board plane is substantially parallel to the pivot axis.

7. The computed tomography device of claim 6, wherein the board plane is substantially perpendicular to the system axis based on the board being in the preparation position of the board.

8. The computed tomography device of claim 1, wherein the board projects away from the opening when the board is in the examination position of the board.

9. The computed tomography device of claim 1, wherein the first pivoting movement of the board about the pivot axis causes the board to be lowered.

10. The computed tomography device of claim 1, wherein the body support apparatus includes a holding apparatus;

the pivoting apparatus is connected to the gantry via the holding apparatus;

the board is connected to the holding apparatus via the pivoting apparatus, the board being mounted pivotably about the pivot axis relative to the holding apparatus; and the holding apparatus is configured to adjustably set a distance between the pivot axis and the system axis.

11. The computed tomography device of claim 1, wherein the gantry includes a first gantry part and a second gantry part, the first gantry part including a rotatably mounted rotor with a projection data acquisition system, and the second gantry part including at least one section of the opening;

the board is connected to the second gantry part via the pivoting apparatus, the board being mounted pivotably about the pivot axis relative to the second gantry part; and the first gantry part is mounted movably relative to the second gantry part such that a translatory movement of the first gantry part relative to the second gantry part is executable while, the second gantry part rests relative to the head of the person, and the body support apparatus rests relative to the head of the person and relative to the at least one section of the opening contemporaneously with the head of the person being located in the opening.

12. A medical imaging system comprising:

the computed tomography device of claim 1; and a patient bed configured to support the person, the patient bed being arrangeable in an examination position of the patient bed relative to the gantry.

13. The medical imaging system of claim 12, wherein the board is configured to bridges a gap extending between the gantry and the patient bed substantially perpendicular to the system axis based on the patient bed being in the examination position of the patient bed and the board being in the examination position of the board.

14. The medical imaging system of claim 12, wherein the body support apparatus is arranged relative to the gantry such that the bed-side edge of the board is configured to rests on the patient bed based on the patient bed being in the examination position of the patient bed and the board being in the examination position of the board.

15. A method for arranging the board of the body support apparatus relative to the gantry of the computed tomography device of claim 1, the method comprising:

moving the board relative to the gantry from the preparation position of the board to the examination position of the board via the first pivoting movement of the board about the pivot axis.

16. The computed tomography device of claim 7, wherein the board projects away from the opening when the board is in the examination position of the board.

17. The computed tomography device of claim 16, wherein the first pivoting movement of the board about the pivot axis causes the board to be lowered.

18. The computed tomography device of claim 17, wherein the body support apparatus includes a holding apparatus;

the pivoting apparatus is connected to the gantry via the holding apparatus;

the board is connected to the holding apparatus via the pivoting apparatus, the board being mounted pivotably about the pivot axis relative to the holding apparatus; and the holding apparatus is configured to adjustably set a distance between the pivot axis and the system axis.

19. The computed tomography device of claim 18, wherein the gantry includes a first gantry part and a second gantry part, the first gantry part including a rotatably mounted rotor with a projection data acquisition system, and the second gantry part including at least one section of the opening;

the board is connected to the second gantry part via the pivoting apparatus, the board being mounted pivotably about the pivot axis relative to the second gantry part; and the first gantry part is mounted movably relative to the second gantry part such that a translatory movement of the first gantry part relative to the second gantry part is executable while, the second gantry part rests relative to the head of the person, and the body support apparatus rests relative to the head of the person and relative to the at least one section of the opening contemporaneously with the head of the person being located in the opening.

20. The computed tomography device of claim 2, wherein the body support apparatus includes a damper configured to brake the first pivoting movement of the board.

* * * * *